United States Patent [19]
Kurogi et al.

[11] Patent Number: 5,624,918
[45] Date of Patent: Apr. 29, 1997

[54] PHOSPHONIC DIESTER DERIVATIVES

[75] Inventors: Yasuhisa Kurogi; Kazuyoshi Miyata; Shizuo Nakamura; Mitsuyoshi Kondo, all of Naruto; Takeshi Iwamoto, Komatsushima; Chieko Naba, Naruto; Yoshihiko Tsuda, Naruto; Yasuhide Inoue, Naruto; Jun Kanaya; Keigo Sato, both of Tokushima-ken, all of Japan

[73] Assignee: Otsuka Pharmaceutical Factory, Inc., Tokushima, Japan

[21] Appl. No.: 387,907

[22] PCT Filed: May 31, 1994

[86] PCT No.: PCT/JP94/00883

§ 371 Date: Feb. 15, 1995

§ 102(e) Date: Feb. 15, 1995

[87] PCT Pub. No.: WO95/00524

PCT Pub. Date: Jan. 5, 1995

[30] Foreign Application Priority Data

Jun. 17, 1993 [JP] Japan ..................... 5-146528

[51] Int. Cl.$^6$ ........................ A61K 31/675; C07F 9/6512
[52] U.S. Cl. ................. 514/80; 540/542; 544/92; 544/244
[58] Field of Search ................... 544/244, 243; 540/542; 514/80

[56] References Cited

U.S. PATENT DOCUMENTS

| | | | |
|---|---|---|---|
| 4,232,010 | 11/1980 | Tsukamoto et al. | 424/200 |
| 4,434,162 | 2/1984 | Tsukamoto et al. | 424/200 |
| 4,822,780 | 4/1989 | Tsuda et al. | 514/119 |
| 4,971,957 | 11/1990 | Tsutsumi et al. | 514/79 |
| 5,081,112 | 1/1992 | Tsutsumi et al. | 514/119 |

FOREIGN PATENT DOCUMENTS 0402033  12/1990  European Pat. Off. .

OTHER PUBLICATIONS

Otsuka Seiyaku Kogyo KK Derwent Abstract of JP 02–11590 (Jan. 1990).
Otsuka Pharm. Co. Derwent Abstract of JP 03–236394A (Oct. 1991).
Otsuka Pharm. Co. Derwent Abstract of JP 04–243888A (Aug. 1992).
Otsuka Seiyaku Kogyo KK Derwent Abstract of JP 04–244090 (Sep. 1992).
Otsuka Seiyaku Kogyo KK Derwent Abstract of JP 04–356495A (Dec. 1992).
Otsuka Seiyaku Kogyo KK Derwent Abstract of JP 05–43589A (Feb. 1993).
Otsuka Seiyaku Kogyo KK Derwent Abstract of JP 05–97883A (Apr. 1993).
Tsutsumi et al., *Chemical Abstracts*, vol. 113, No. 6602, Abstract for JP 02,11,590 (Jan. 16, 1990).
Dia et al., *Chemical Abstracts*, vol. 116, No. 99337, Abstract for JP 03,236,394 (Oct. 22, 1991).
Shoji et al., *Chemical Abstracts*, vol. 118, No. 38912, Abstract for JP 04,243,888 (Jan. 24, 1991).
Myata et al., *Chemical Abstracts*, vol. 118, No. 7195 Abstract for JP 04,244,090 (Oct. 1, 1992).
Myata et al., *Chemical Abstracts*, vol. 119, No. 95360 Abstract for JP 05,43,589 (Feb. 23, 1993).
Tsuda et al., *Chemical Abstracts*, vol. 119, No. 95829 Abstract for JP 04,356,495 (Dec. 10, 1992).
Myata et al. *Chemical Abstracts*, vol. 119, No. 160570 Abstract for JP 05,97,883 (Apr. 20, 1993).

*Primary Examiner*—Sharon Gibson
*Assistant Examiner*—Richard S. Myers
*Attorney, Agent, or Firm*—Sughrue, Mion, Zinn, Macpeak & Seas

[57] ABSTRACT

The present invention provides a phosphonic diester derivative of the following general formula (1):

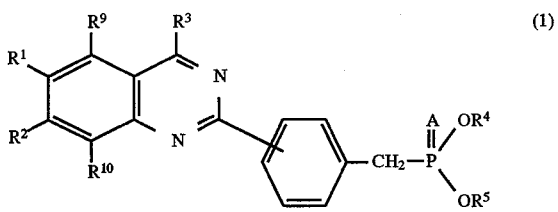

wherein A represents an oxygen atom or a sulfur atom; $R^1$, $R^2$, $R^9$ and $R^{10}$ are the same or different and they each represent a hydrogen atom, a lower alkoxy group, a nitro group, a lower alkyl group, a halogen-substituted lower alkyl group or a halogen atom; $R^3$ represents a phenyl group, —B—$R^6$ (wherein B represents an oxygen atom or a sulfur atom and $R^6$ represents a hydrogen atom, a lower alkyl group, a cycloalkyl group, a phenyl group, a phenyl(lower) alkyl group optionally having a halogen atom as a substituent on the phenyl ring, a phenoxy(lower)alkyl group, a lower alkoxycarbonyl(lower)alkyl group, a carboxy(lower)alkyl group or a lower alkenyl group) or —$NR^7R^8$ (wherein $R^7$ and $R^8$ and are the same or different and they each represent a hydrogen atom, a lower alkyl group, an amino group or a cycloalkyl group or combinedly represent a lower alkylene group); and $R^4$ and $R^5$ are the same or different and they each represent a hydrogen atom or a lower alkyl group.

The derivative of the present invention is useful as therapeutic agents for hyperlipidemic diseases, hypertension, diabetes and the like.

8 Claims, No Drawings

PHOSPHONIC DIESTER DERIVATIVES

This application is a National Phase filing of PCT/JP94/00883, which was filed in the International Phase May 31, 1994.

TECHNICAL FIELD

The present invention relates to novel phosphonic diester derivatives.

PRIOR ART

The phosphonic diester derivatives of the invention are novel compounds not heretofore described in the literature.

The object of the invention is to provide compounds of value as medicines as will be described hereinafter.

DISCLOSURE OF THE INVENTION

The present invention provides a phosphonic diester derivative of the following general formula (1):

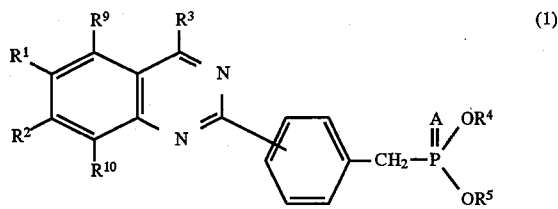

wherein A represents an oxygen atom or a sulfur atom; $R^1$, $R^2$, $R^9$ and $R^{10}$ are the same or different and they each represent a hydrogen atom, a lower alkoxy group, a nitro group, a lower alkyl group, a halogen-substituted lower alkyl group or a halogen atom; $R^3$ represents a phenyl group, —B—$R^6$ (wherein B represents an oxygen atom or a sulfur atom and $R^6$ represents a hydrogen atom, a lower alkyl group, a cycloalkyl group, a phenyl group, a phenyl(lower)alkyl group optionally having a halogen atom as a substituent on the phenyl ring, a phenoxy(lower)alkyl group, a lower alkoxycarbonyl(lower)alkyl group, a carboxy(lower)alkyl group or a lower alkenyl group) or —$NR^7R^8$ (wherein $R^7$ and $R^8$ are the same or different and they each represent a hydrogen atom, a lower alkyl group, an amino group or a cycloalkyl group or combinedly represent a lower alkylene group); and $R^4$ and $R^5$ are the same or different and they each represent a hydrogen atom or a lower alkyl group.

Each of the groups relevant to the above general formula (1) includes the following exemplary species.

The lower alkyl group includes straight- or branched-chain lower alkyl groups such as methyl, ethyl, propyl, isopropyl, butyl, isobutyl, tert-butyl, pentyl, hexyl and so on.

The cycloalkyl group includes cyclopropyl, cyclobutyl, cyclopentyl, cyclohexyl, cycloheptyl, cyclooctyl and so on.

The lower alkoxy group includes methoxy, ethoxy, propoxy, butoxy, pentyloxy, hexyloxy and so on.

The phenyl(lower)alkyl group optionally having a halogen atom as a substituent on the phenyl ring includes benzyl, α-phenetyl, β-phenetyl, 3-phenylpropyl, 4-phenylbutyl, 5-phenylpentyl, 6-phenylhexyl, 2-bromobenzyl, 2-fluorobenzyl, 2-chlorobenzyl, 2-iodobenzyl, 3-bromobenzyl, 3-fluorobenzyl, 3-chlorobenzyl, 3-iodobenzyl, 4-bromobenzyl, 4-fluorobenzyl, 4-chlorobenzyl, 4-iodobenzyl, 4-bromo-3-fluorobenzyl, 4-bromo-2-fluorobenzyl, 3-bromo-4-fluorobenzyl, 2-bromo-4-fluorobenzyl, 4-bromo-3-chlorobenzyl, 4-bromo-2-chlorobenzyl, 3-bromo-4-chlorobenzyl, 2-bromo-4-chlorobenzyl, 4-bromo-3-iodobenzyl, 4-bromo-2-iodobenzyl, 3-bromo-4-iodobenzyl, 2-bromo-4-iodobenzyl, 4-bromo-3-fluoro-α-phenetyl, 4-bromo-3-fluoro-β-phenetyl, 3-(4-bromo-3-fluorophenyl)propyl, 4-(4-bromo-2-fluorophenyl)butyl, 5-(4-bromo-3-fluorophenyl)pentyl, 6-(4-bromo-2-fluorophenyl)hexyl and so on.

The phenoxy(lower)alkyl group includes phenoxymethyl, 2-phenoxyethyl, 3-phenoxylpropyl, 4-phenoxybutyl, 5-phenoxypentyl, 6-phenoxyhexyl and so on.

The lower alkylene group includes methylene, ethylene, trimethylene, tetramethylene, pentamethylene, hexamethylene and so on.

The halogen-substituted lower alkyl group includes chloromethyl, bromomethyl, fluoromethyl, iodomethyl, dichloromethyl, dibromomethyl, difluoromethyl, diiodomethyl, trichloromethyl, tribromomethyl, trifluoromethyl, triiodomethyl, 2,2-difluoroethyl, 2,2,2-trifluoroethyl, 3-bromopropyl, 4,4-dichlorobutyl, 5,5,5-trifluoropentyl, 6-iodohexyl and so on.

The lower alkoxycarbonyl(lower)alkyl group includes methoxycarbonylmethyl, ethoxycarbonylmethyl, propoxycarbonylmethyl, butoxycarbonylmethyl, pentyloxycarbonylmethyl, hexyloxycarbonylmethyl, 1-(methoxycarbonyl)ethyl, 2-(methoxycarbonyl)ethyl, 3-(methoxycarbonyl)propyl, 4-(methoxycarbonyl)butyl, 5-(methoxycarbonyl)pentyl, 6-(methoxycarbonyl)hexyl, 1-(ethoxycarbonyl)ethyl, 2-(ethoxycarbonyl)ethyl, 3-(ethoxycarbonyl)propyl, 4-(ethoxycarbonyl)butyl, 5-(ethoxycarbonyl)pentyl, 6-(ethoxycarbonyl)hexyl and so on.

The carboxy(lower)alkyl group includes carboxymethyl, 1-carboxyethyl, 2-carboxyethyl, 1-carboxypropyl, 2-carboxypropyl, 3-carboxypropyl, 1-carboxybutyl, 2-carboxybutyl, 3-carboxybutyl, 4-carboxybutyl, carboxy-t-butyl, 4-carboxypentyl, 5-carboxypentyl, 6-carboxyhexyl and so on.

The lower alkenyl group includes ethenyl, 1-propenyl, 2-propenyl, 2-methyl-2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl and so on.

The halogen atom includes fluorine, chlorine, bromine and iodine.

Among the phosphonic diester derivatives of the formula (1) according to the present invention, those of the following formula (1') are suitable.

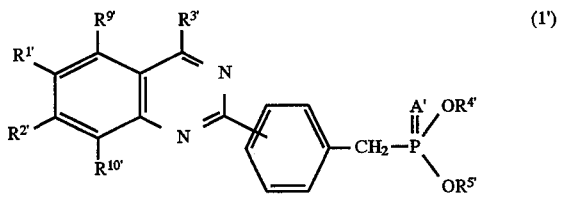

wherein A' represents an oxygen atom or a sulfur atom; $R^{1'}$ represents a hydrogen atom, a lower alkoxy group, a nitro group or a halogen atom; $R^{2'}$ represents a hydrogen atom, a lower alkoxy group, a lower alkyl group, a halogen-substituted lower alkyl group or a halogen atom; $R^{3'}$ represents a phenyl group, —O—$R^6$ (wherein $R^6$ is as defined in the formula (1)), —S—$R^{6'}$ (wherein $R^{6'}$ represents a hydrogen atom, a lower alkyl group or a phenyl group) or —$NR^7R^8$ (wherein $R^7$ and $R^8$ are as defined in the formula (1)); $R^{4'}$ represents a lower alkyl group; $R^{5'}$ represents a hydrogen atom or a lower alkyl group; $R^{9'}$ represents a hydrogen atom or a halogen atom; and $R^{10'}$ represents a hydrogen atom or a lower alkoxy group.

The phosphonic diester derivative of the formula (1) according to the invention has excellent hypolipidemic, vasodepressor and hypoglycemic activities and is useful as therapeutic agents for hyperlipidemic diseases, hypertension, diabetes or the like. More specifically, the derivative can treat or prevent various types of diseases (hyperlipidemic diseases) such as hypercholesterolemia, hypertriglyceridemia, hyperphospholipidemia and hyper-free fatty acidemia, hypertension and diabetes.

Examples of preferable derivatives of the present invention as the active ingredient of therapeutic agents for hyperlipidemic diseases, etc. are those of the formula (1') wherein $R^{1'}$ and $R^{2'}$ each represent a lower alkoxy group; $R^{3'}$ represents —O—$R^6$ (wherein $R^6$ is as defined above); A' represents an oxygen atom; and $R^{4'}$ and $R^{5'}$ each represent a lower alkyl group.

Examples of such derivatives also include those of the formula (1') wherein $R^{9'}$ and $R^{10'}$ each represent a hydrogen atom; and $R^{3'}$ represents a hydroxy group, a lower alkoxy group, a phenyl(lower)alkoxy group or a lower alkenyloxy group.

Specific examples of these preferred derivatives of the invention include the following compounds (1)–(6). Among them the most preferred derivatives of the invention are compounds (3) and (4), which produce excellent pharmacological effects.

(1) Diethyl 4-(4-hydroxy-6,7-dimethoxyquinazolin-2-yl) benzylphosphonate, (2) diisopropyl 4-(4-hydroxy-6,7-dimethoxyquinazolin-2-yl)benzylphosphonate, (3) diethyl 4-(4,6,7-trimethoxyquinazolin-2-yl) benzylphosphonate, (4) diisopropyl 4-(4,6,7-trimethoxyquinazolin-2-yl) benzylphosphonate, (5) diethyl 4-(4-benzyloxy-6,7-dimethoxyquinazolin-2-yl) benzylphosphonate, and (6) diethyl 4-(4-allyloxy-6,7-dimethoxyquinazolin-2-yl) benzylphosphonate.

The phosphonic diester derivative of the formula (1) according to the invention can be produced by several different processes. Some exemplary processes are schematically shown hereunder.

[Reaction Schema-1]

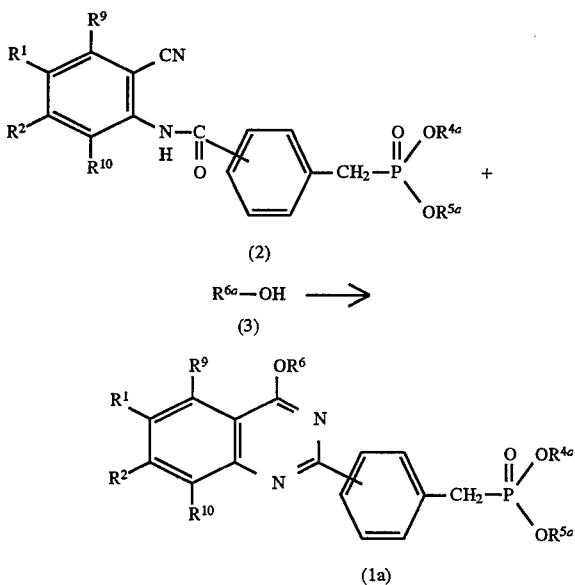

wherein $R^1$, $R^2$, $R^6$, $R^9$ and $R^{10}$ are as defined above; $R^{6a}$ represents a lower alkyl group, a cycloalkyl group, a phenyl group, a phenyl(lower)alkyl group optionally having a halogen atom as a substituent on the phenyl ring, a phenoxy (lower)alkyl group or a lower alkenyl group; and $R^{4a}$ and $R^{5a}$ are the same or different and they each represent a lower alkyl group.

According to the process shown Reaction Schema-1, the compound (1a) of the invention can be prepared by reacting the compound (2) with the alcohol (3) in the presence of an acid catalysts such as p-toluenesulfonic acid, benzenesulfonic acid, ammonium chloride and camporsulfonic acid, without using a solvent or in an inert solvent such as benzene, tetrahydrofuran (THF) and toluene. The alcohol (3) is generally used in an equimolar to large excess proportion relative to the compound (2). The amount of the acid catalyst is generally about 0.3 to 1 mole per mole of the compound (2). The reaction can be carried out at room temperature to the reflux temperature of the solvent for about 1–20 hours.

The compound (1a) might be obtained as a mixture of the compound of the formula (1a) wherein $R^6$=H and the compound of the formula (1a) wherein $R^6$=$R^{6a}$ ($\neq$H). The compounds can be easily isolated by conventional separation and purification procedures as will be described later.

[Reaction Schema-2]

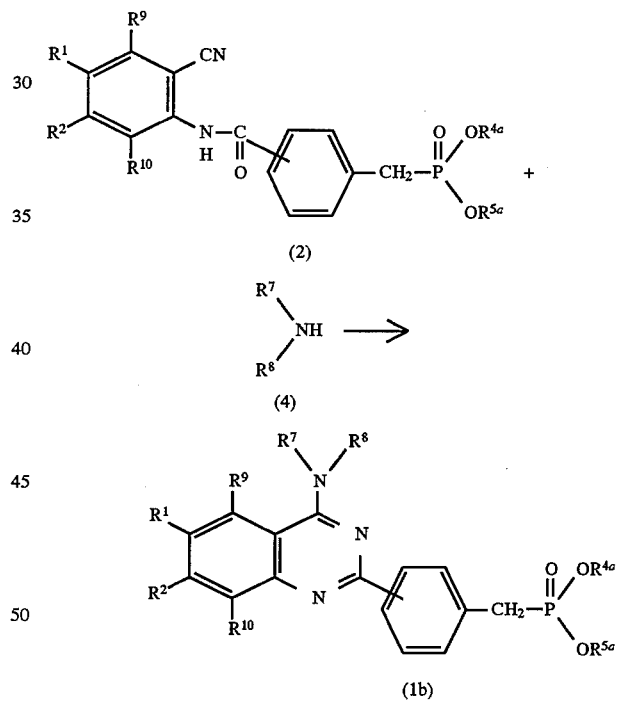

wherein $R^1$, $R^2$, $R^{4a}$, $R^{5a}$, $R^7$, $R^8$, $R^9$ and $R^{10}$ are as defined above.

According to the process shown in Reaction Schema-2, the compound (1b) of the invention can be prepared by reacting the compound (2) with an amine (4) without using a solvent or in an inert solvent such as benzene, xylene, THF, 1,4-dioxane and toluene. The amine (4) is preferably used in an equimolar to small excess proportion relative to the compound (2). As the amine (4), a 40–70% aqueous amine solution can be also used. The reaction is carried out at room temperature to the reflux temperature of the solvent for about 1–20 hours.

[Reaction Schema-3]

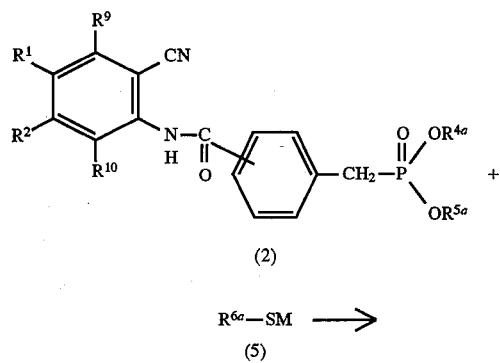

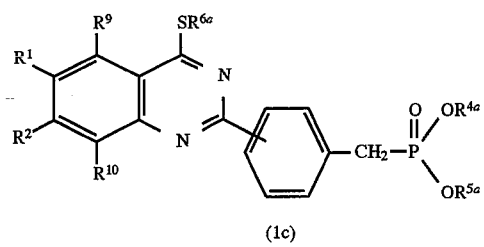

wherein $R^1$, $R^2$, $R^{4a}$, $R^{5a}$, $R^{6a}$, $R^9$ and $R^{10}$ are as defined above; and M represents a hydrogen atom or an alkali metal atom.

As shown in Reaction Schema-3, the compound (2) can be converted to the compound (1c) of the invention by reacting the compound (2) with a thiol (5) in the presence of an alkali such as sodium hydroxide, potassium hydroxide and sodium hydride in an inert solvent such as benzene, xylene, THF, 1,4-dioxane and toluene. The thiol (5) is preferably used in an equimolar to excess proportion relative to the compound (2). The alkali is preferably used in an equimolar to small excess proportion relative to the compound (2). In this reaction, as the thiol (5), a 1–30% aqueous alkali metal salt solution can be also used. The reaction is carried out at room temperature to the reflux temperature of the solvent for about 1–30 hours.

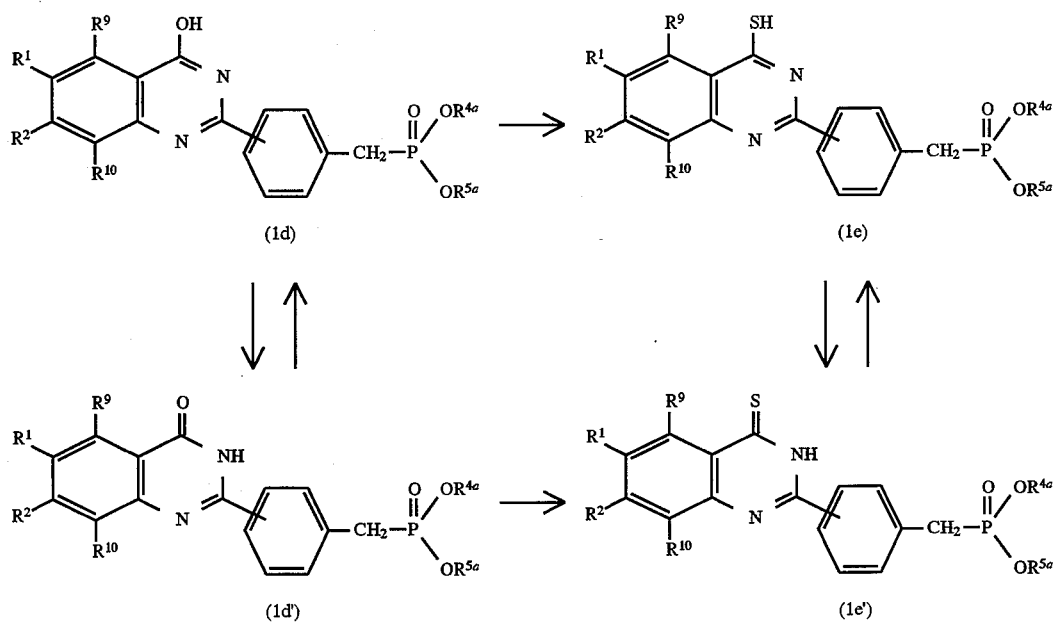

[Reaction Schema-4']

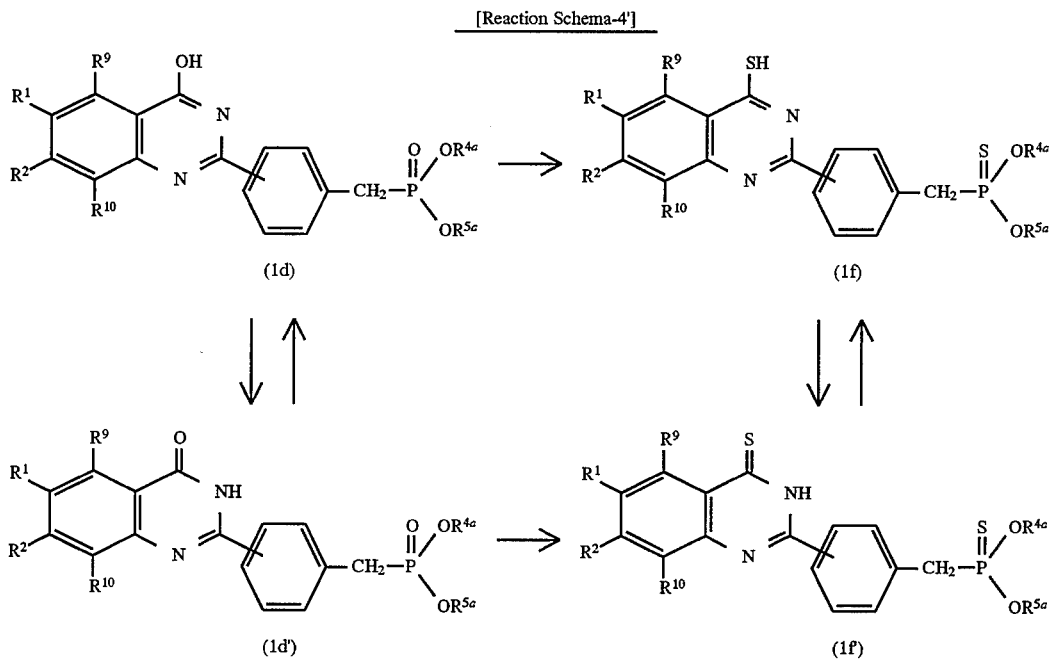

wherein $R^1$, $R^2$, $R^{4a}$, $R^{5a}$, $R^9$ and $R^{10}$ are as defined above As shown in Reaction Schema-4, the compound (1d) of the invention can be converted to the compound (1e) by treating the compound (1d) with a sulfur-containing reagent such as Lawesson's reagent [2,4-bis(4-methoxyphenyl)-1,3-dithia-2,4-diphosphethane-2,4-disulfide] and diphosphorus pentasulfide. The reaction is carried out using about one equivalent of the sulfur-containing reagent relative to the compound (1d) in an inert solvent such as benzene, toluene, xylene and acetonitrile at the reflux temperature of the solvent for about 5–30 hours.

As shown in Reaction Schema-4', the compound (1d) of the invention can be converted to the compound (1f) by treating the compound (1d) with at least two equivalents of the sulfur-containing reagent. The reaction solvent and reaction conditions are similar to those used in the reaction of Reaction Schema-4.

The compounds (1d), (1e) and (1f) in the Reaction Schemata-4 and -4' may exist as tautomers (1d'), (1e') and (1f'), which, of course, are subsumed in the concept of the compound of the invention.

[Reaction Schema-5]

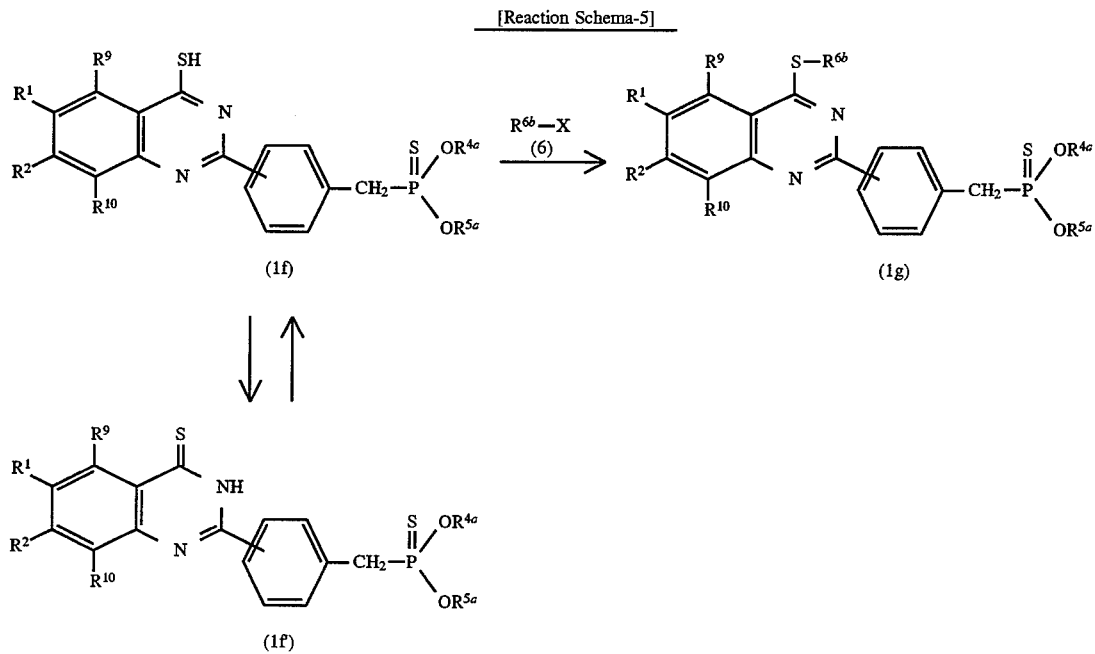

wherein $R^1$, $R^2$, $R^{4a}$, $R^{5a}$, $R^9$ and $R^{10}$ are as defined above; and $R^{6b}$ represents a lower alkyl group, a cycloalkyl group, a phenyl(lower)alkyl group optionally having a halogen atom as a substituent on the phenyl ring, a lower alkoxycarbonyl(lower)alkyl group, a carboxy(lower)alkyl group or a lower alkenyl group; and X represents a halogen atom.

As shown in Reaction Schema-5, the compounds (1f) and (1f') can be converted to the compound (1g) of the invention by reacting the compound (1f) or (1f') with the compound (6) in the presence of a base such as pyridine, collidine, lutidine, triethylamine and N,N-diethylaniline in an inert solvent such as benzene, toluene, xylene, THF and 1,4-dioxane. The compound (6) is preferably used in an equimolar to small excess proportion relative to the compound (1f). The reaction is carried out at room temperature to the reflux temperature of the solvent for about 1–20 hours.

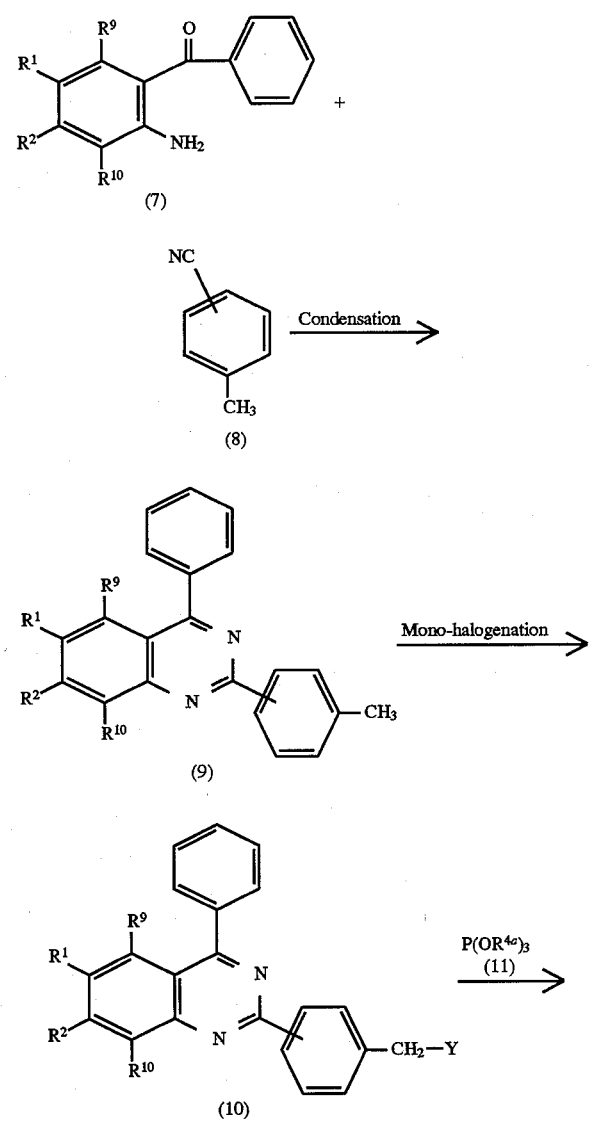

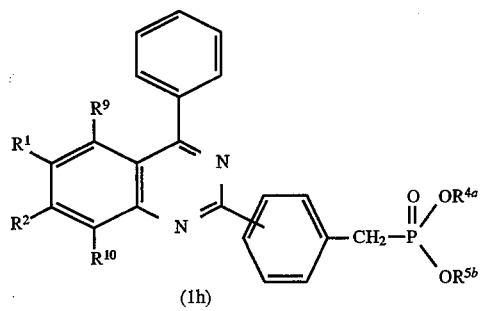

wherein $R^1$, $R^2$, $R^{4a}$, $R^9$ and $R^{10}$ are as defined above; $R^{5b}$ is the same as $R^{4a}$; and Y represents a halogen atom.

In Reaction Schema-6, the condensation reaction of 2-aminobenzophenone derivative (7) and benzonitrile derivative (8) is carried out in the presence of a strong base such as sodium hydride, potassium hydride and sodium amide in an inert solvent such as THF, 1,2-dimethoxyethane, and N,N-dimethylformamide (DMF) at room temperature to the reflux temperature of the solvent for about 0.5–5 hours. The benzonitrile derivative (8) is preferably used in an approximately equimolar proportion relative to the 2-aminobenzophenone derivative (7). The strong base is preferably used in an equimolar to small excess proportion relative to the 2-aminobenzophenone derivative (7).

The monohalogenation reaction of the compound (9) can be carried out using a halogenating agent such as N-bromo-succinimide (NBS), N-chloro-succinimide (NCS) and bromine in the presence of a catalyst such as benzoyl peroxide, α,α'-azobisisobutyronitrile (AIBN) in an inert solvent such as benzene and carbon tetrachloride. The amount of the halogenating agent is generally one equivalent to small excess relative to the compound (9). The reaction is carried out at about 50° C. to the reflux temperature of the solvent for 2–20 hours.

The objective compound (1h) can be obtained by reacting the resultant monohalide (10) with the trialkyl phosphite (11). The reaction is preferably carried out without using any solvent, though it can be done in an inert solvent, e.g. lower alcohols such as methanol and ethanol, aromatic hydrocarbons such as benzene, toluene and xylene, and DMF. The trialkyl phosphite (11) is used in an approximately equimolar proportion to five moles per mole of the monohalide (10). The reaction is generally carried out at 100°–180° C. for about 0.5–3 hours, of which condition varies depending on the monohalide (10).

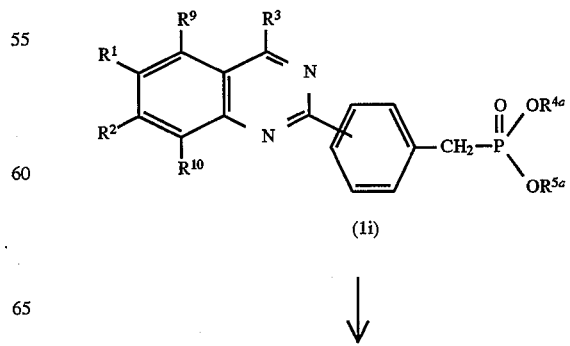

-continued
[Reaction Schema-7]

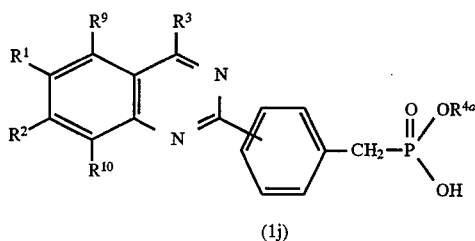

(1j)

wherein $R^1$, $R^2$, $R^3$, $R^{4a}$, $R^{5a}$, $R^9$ and $R^{10}$ are as defined above.

According to the process shown in Reaction Schema-7, the objective partially hydrolysed compound (1j) can be obtained by reacting the compound (1i) with a lithium halide such as lithium bromide, lithium chloride and lithium iodide and subsequently treating the reaction mixture with an aqueous solution of mineral acid such as hydrochloric acid and sulfuric acid. The reaction is carried out using a lithium halide in an amount of at least five moles per mole of the compound (1i) in an inert solvent such as acetonitrile and DMF at room temperature to the reflux temperature of the solvent for 5–24 hours.

The starting compound (2) in the reaction schemata-1 to -3 can be prepared, for example, by the process described in Japanese Unexamined Patent Publication No. 151199/1986.

wherein $R^1$, $R^2$, $R^{4a}$, $R^{5a}$, $R^{6b}$, $R^9$, $R^{10}$ and X are as defined above.

As shown in Reaction Schema-8, the compounds (1d) and (1d') can be converted to the compound (1k) of the invention by reacting the compound (1d) or (1d') with the compound (6) in the presence of a base such as metal sodium, metal potassium, potassium t-butoxide, sodium methoxide and sodium ethoxide in an inert solvent such as methanol and propanol. The compound (6) is preferably used in an equimolar to small excess proportion relative to the starting compound. The amount of the base is preferably about one equivalent relative to the starting compound. The reaction is carried out at room temperature to the reflux temperature of the solvent for about 1–24 hours. The compound (12) is obtained as a by-product in some cases.

[Reaction Schema-8]

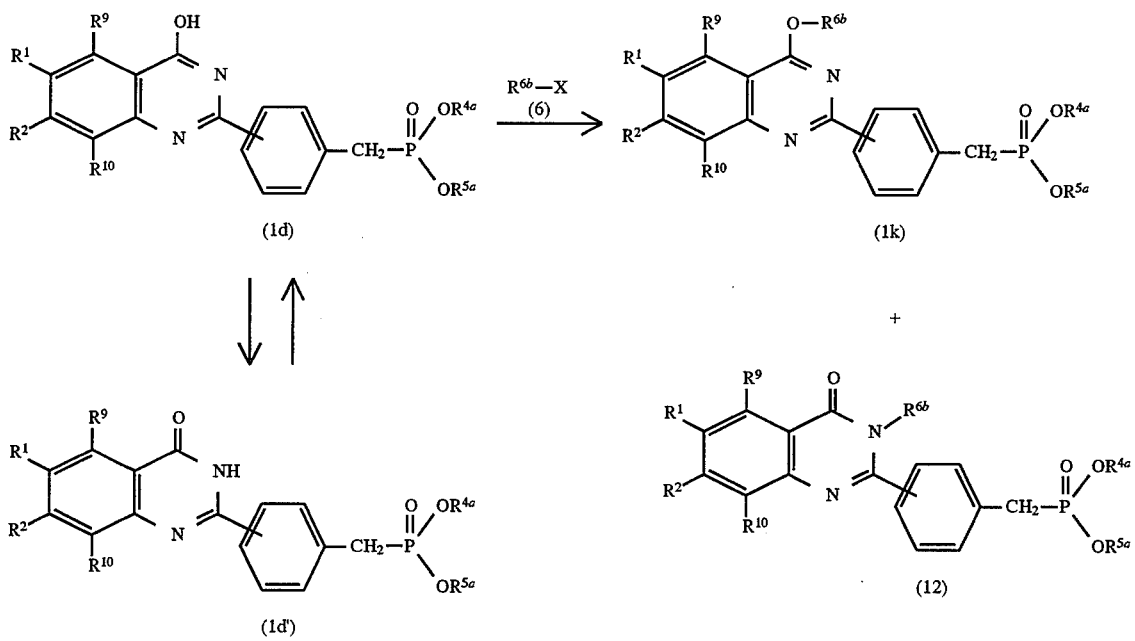

[Reaction Schema-9]
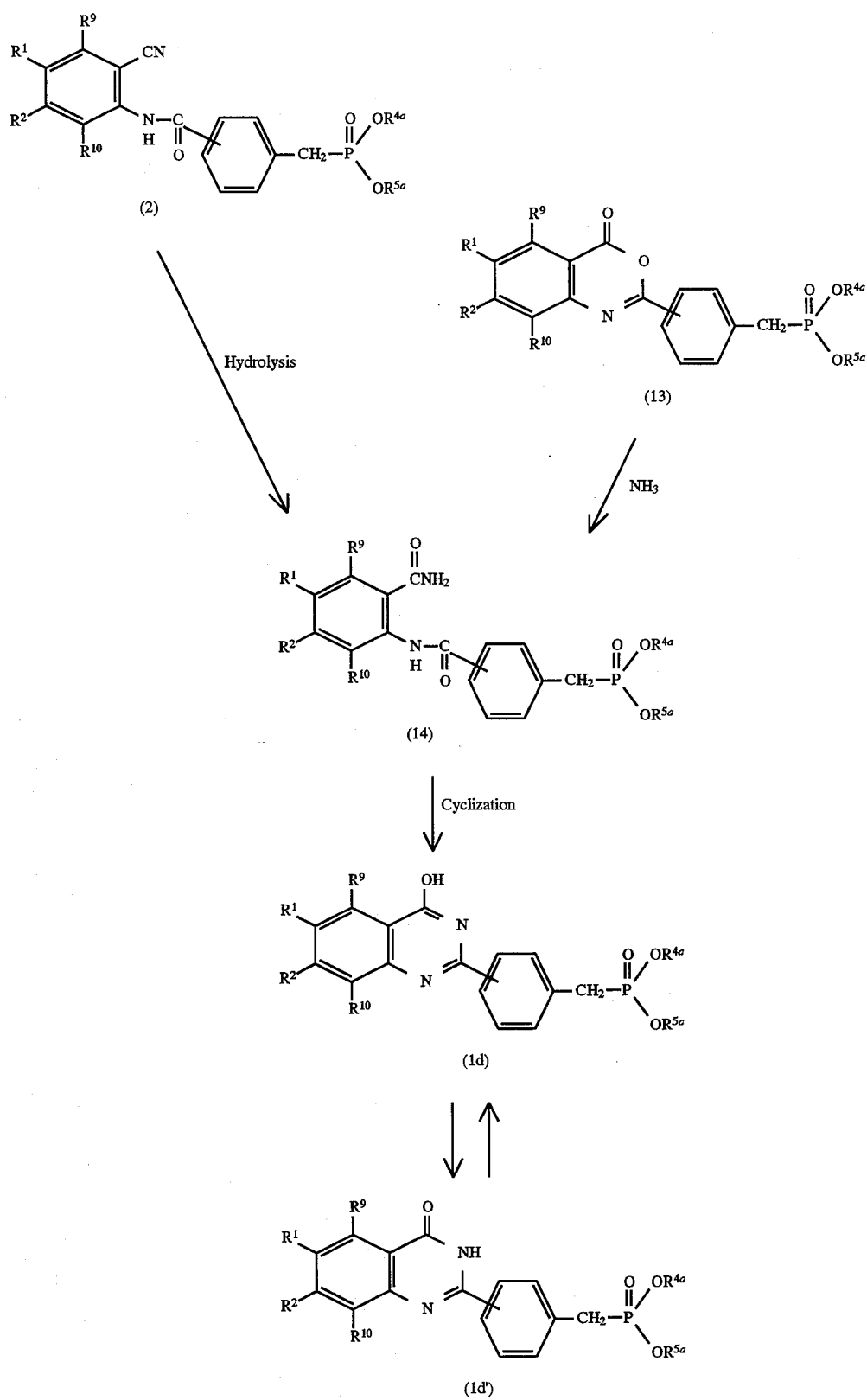
wherein $R^1$, $R^2$, $R^{4a}$, $R^{5a}$, $R^9$ and $R^{10}$ are as defined above.
The compounds (1d) and (1d') can be obtained by the process shown in the reaction schema-9 as well. More specifically, the objective compound can be obtained by either hydrolysing the compound (2) or treating the compound (13) with ammonia, and subjecting the resultant compound (14) to cyclization reaction.

The hydrolysis reaction of the compound (2) is carried out in the presence of a base catalyst such as sodium hydroxide and potassium hydroxide using an about 10–30% aqueous hydrogen peroxide solution without using a solvent or in an inert solvent such as THF, methanol and 1,4-dioxane. The hydrogen peroxide is generally used in an equimolar proportion to about ten moles per mole of the compound (2). The base catalyst is generally used in an equimolar to small excess proportion relative to the compound (2). The reaction is carried out at room temperature to the reflux temperature of the solvent for about 2–20 hours.

On the other hand, the conversion of the compound (13) to the compound (14) by the treatment with ammonia can be carried out by allowing the compound (13) and an excess amount of aqueous ammonia to stand in an inert solvent such as methanol, ethanol and THF at 0° C. to room temperature for about 0.5–10 hours.

The cyclization reaction of the compound (14) obtained by one of the above reactions can be carried out using about 1–6N aqueous alkali solution such as sodium hydroxide and potassium hydroxide in an inert solvent such as lower alcohols and 1,4-dioxane. The aqueous alkali solution is preferably used in an equimolar to small excess proportion relative to the compound (14). The reaction is carried out at room temperature to the reflux temperature of the solvent for about 1–10 hours.

The compound (13) in the above reaction can be prepared, for example, by the process described in Japanese Unexamined Patent Publication No. 9670/1994.

The objective compound in each of the above processes can be easily isolated and purified by conventional separation procedures. Such procedures include adsorption chromatography, preparative thin-layer chromatography, recrystallization, solvent extraction and so on.

Using suitable pharmaceutically acceptable carriers, the compound of the invention is made into pharmaceutical compositions for use. Useful pharmaceutically acceptable carriers include various conventional diluents or excipients such as fillers, volume builders, binders, humectants, disintegrators, surfactants, lubricants, etc. and are selectively employed to the desired unit dosage form.

The above pharmaceutical composition can be provided in a variety of unit dosage forms according to the intended medical treatment. Typical examples are tablets, pills, powders, solutions, suspensions, emulsions, granules, capsules, suppositories, injections (solutions, suspensions, etc.) and eye-drops.

The molding of tablets can be made using, as said pharmaceutically acceptable carriers, an excipient such as lactose, sucrose, sodium chloride, glucose, urea, starch, calcium carbonate, kaolin, crystalline cellulose, silicic acid, potassium phosphate, etc., a binder such as water, ethanol, propanol, simple syrup, glucose syrup, starch solution, gelatin solution, carboxymethyl cellulose, hydroxypropyl cellulose, methylcellulose, polyvinylpyrrolidone, etc., a disintegrator such as carboxymethyl cellulose sodium, carboxymethyl cellulose calcium, low-substituted hydroxypropyl cellulose, dry starch, sodium alginate, agar powder, laminaran powder, sodium hydrogen carbonate, calcium carbonate, etc., a surfactant such as polyoxyethylene sorbitan fatty acid ester, sodium lauryl sulfate, stearyl monoglyceride, etc., a disintegration inhibitor such as sucrose, stearin, cacao butter, hydrogenated oil, etc., an absorption promoter such as quaternary ammonium bases, sodium lauryl sulfate, etc., a humectant such as glycerin, starch, etc., an adsorbent such as starch, lactose, kaolin, bentonite, colloidal silica, etc., and a lubricant such as purified talc, salts of stearic acid, boric acid powder, polyethylene glycol and so on. Furthermore, such tablets can be coated, if necessary, to provide sugar-coated tablets, gelatin-coated tablets, enteric tablets, film-coated tablets, etc. or be processed into double-layer or multiple-layer tablets.

In the manufacture of pills, various excipients such as glucose, lactose, starch, cacao butter, hydrogenated vegetable oil, kaolin, talc, etc., binders such as gum arabic powder, tragacanth powder, gelatin, ethanol, etc. and disintegrators such as laminaran, starch, etc. can be employed as the pharmaceutically acceptable carrier.

The suppositories can be manufactured using polyethylene glycol, cacao butter, higher alcohols or their esters, gelatin, semisynthetic glycerides, etc. as the carrier.

The capsules can be manufactured in the conventional manner by blending the compound of the invention with any of the various pharmaceutically acceptable carriers mentioned above and filling the resulting composition into hard gelatin capsule shells, soft capsule shells or the like.

When the compound of the invention is to be provided in an injectable form such as a solution, emulsion or suspension, the preparation is preferably sterilized and rendered isotonic with respect to the blood. As the diluent for use in such a preparation, water, ethyl alcohol, macrogol, propylene glycol, ethoxylated isostearyl alcohol, polyoxyisostearyl alcohol, polyoxyethylene sorbitan fatty acid ester, etc. can be employed. In this operation, a sufficient amount of sodium chloride, glucose or glycerin may be added to the composition to provide an isotonic solution. Conventional solubilizers, buffers, local anesthetics, etc. can be also added.

The eye-drops can be manufactured in the conventional manner using sterile distilled water as the vehicle, sodium dihydrogen phosphate and/or sodium monohydrogen phosphate, for instance, as the buffer, sodium chloride or the like as the isotonizing agent, and benzalkonium chloride, chlorobutanol or the like as the antimicrobial agent.

Further, coloring agents, preservatives, perfumes, flavors, sweeteners, or other pharmacologically active substances can be optionally incorporated in the compositions in the various dosage forms mentioned above.

There is no particular limitation on the administration method for the pharmaceutical composition of the invention. Thus, the proper method can be determined according to the particular dosage form, patient's age, sex and other characteristics, severity of disease and other conditions. For example, said tablets, pills, solutions, suspensions, emulsions, granules and capsules are administered by the oral route. The injections are administered singly or in admixture with glucose, amino acid or like conventional infusions by the intravenous route or, if necessary, administered singly by the intramuscular, intradermal, subcutaneous or intraperitoneal route. The suppositories are administered intrarectally and the eye-drops are instilled into the eyes.

The proportion of the compound of the formula (1) of the invention in the pharmaceutical composition is not critical but can be liberally selected from a broad range. It is generally preferable that the compound accounts for about 1 to 70 weight % of the final composition. The dosing amount of the pharmaceutical composition can be selected according to the selected administration method, patient's age, sex and other characteristics, severity of disease and other conditions. The dosage of the compound of the invention as the active ingredient is preferably about 0.05–100 mg per kg body weight a day and this amount can be administered in 1 to 4 divided doses. In preparation of eye-drops, the daily dosage of the active ingredient is preferably selected from the range of about 0.3–2 μg, and the eye-drops are generally applied once a day.

BEST MODE FOR PRACTICING THE INVENTION

Preparation examples and pharmacological test examples for the compound of the invention are given below to clarify the invention in further detail.

EXAMPLE 1

Preparation of diethyl 4-(4-methoxyquinazolin-2-yl)benzylphosphonate
(Process 1)

A 15.7 g portion of anthranilonitrile was dissolved in 50 ml of pyridine. While the solution was stirred under ice-cooling, a solution of 40.7 g of 4-[(diethoxyphosphoryl)-methyl]benzoyl chloride in 50 ml of dry dichloromethane was added dropwise. The stirring was continued at room temperature for 12 hours, after which the reaction mixture was diluted with 200 ml of dichloromethane and washed with diluted hydrochloric acid. The organic layer was dried over anhydrous magnesium sulfate and the solvent was distilled off under reduced pressure. The residue was recrystallized from chloroform-n-hexane to provide 25.9 g of diethyl 4-[N-(2-cyanophenyl)carbamoyl]benzylphosphonate as colorless crystals.
(Process 2)

A 3.7 g quantity of the diethyl 4-[N-(2-cyanophenyl)carbamoyl]benzylphosphonate crystals obtained in Process 1 and 0.8 g of p-toluenesulfonic acid monohydrate were suspended in 100 ml of methanol and heated at 70° C. with stirring for 10 hours. After completion of the reaction, the solvent was distilled off under reduced pressure. The residue was subjected to silica gel column chromatography (eluent: chloroform) and the resulting crude crystals were recrystallized from dichloromethane-n-hexane to provide 1.9 g of the objective compound as colorless crystals. Table 1 shows the structure and physical property (melting point) of the compound thus obtained.

EXAMPLES 2–10

The compounds set forth in Table 1 were prepared in the same manner as in Example 1. Table 1 also shows the structures and physical properties (melting points) of these compounds.

EXAMPLES 11 and 12

Preparation of diisopropyl 4-(6-bromo-4-methoxyquinazolin-2-yl)benzylphosphonate and diisopropyl 4-(6-bromo-4-hydroxyquinazolin-2-yl)benzylphosphonate The reaction was carried out in the same manner as in Example 1 and the crude product was purified by silica gel column chromatography (eluent: chloroform: methanol= 40:1) and 4-methoxyquinazoline was obtained from the former fraction, and 4-hydroxyquinazoline from the latter fraction. Table 1 also shows the structures and physical properties (melting points) of these compounds.

EXAMPLES 13–20

The compounds set forth in Table 1 were prepared in the same manner as in Examples 11 and 12. Table 1 also shows the structures and physical properties (melting points) of these compounds. Table 2 shows the results of $^1$H-NMR analysis of some compounds.

EXAMPLE 21

Preparation of diethyl 4-(4-methylaminoquinazolin-2-yl) benzylphosphonate

A 3.7 g portion of diethyl 4-[N-(2-cyanophenyl)carbamoyl]benzylphosphonate and 10 ml of a 40% aqueous methylamine solution were dissolved in 50 ml of THF and refluxed with heating at 70° C. for 30 hours. After completion of the reaction, the solvent was distilled off under reduced pressure. The residue was subjected to silica gel column chromatography (eluent: chloroform: methanol=100:1) and the crude crystals obtained were recrystallized from chloroform-n-hexane to provide 1.0 g of the objective compound as colorless crystals. Table 1 also shows the structure and physical property (melting point) of the compound thus obtained.

EXAMPLES 22–35

The compounds set forth in Table 1 were prepared in the same manner as in Example 21. Table 1 also shows the structures and physical properties (melting points) of these compounds. Table 2 shows the results of $^1$H-NMR analysis of some compounds.

EXAMPLE 36

Preparation of diethyl 4-(6-bromo-4-ethylthioquinazolin-2-yl)benzylphosphonate

A 4.5 g portion of diethyl 4-[N-(4-bromo-2-cyanophenyl) carbamoyl]benzylphosphonate (obtained in the same manner as in Process 1 of Example 1), 50 ml of ethanethiol and 0.4 g of sodium hydroxide were added to 50 ml of THF and heated with stirring in nitrogen atmosphere at 60° C. for 30 hours. After adding 100 ml of 1N aqueous sodium hydroxide solution, the reaction mixture was extracted with chloroform. The chloroform layer was washed with water, dried over sodium sulfate and concentrated under reduced pressure. The residue was subjected to silica gel column chromatography (eluent: chloroform) and the crude crystals obtained were recrystallized from chloroform-n-hexane to provide 0.8 g of the objective compound as colorless crystals. Table 1 shows the structure and physical property (melting point) of the compound.

EXAMPLES 37–38

The compounds set forth in Table 1 were prepared in the same manner as in Example 36. Table 1 also shows the structures and physical properties (melting points) of these compounds.

EXAMPLE 39

Preparation of diethyl 4-(4-phenylquinazolin-2-yl)benzylphosphonate

A 7.9 g portion of 2-aminobenzophenone, 4.7 g of 4-methylbenzonitrile and 2.0 g of 60% sodium hydride were suspended in 40 ml of THF and heated at 60° C. with stirring for 2 hours. After completion of the reaction, the reaction mixture was allowed to cool and the precipitate was collected by filtration, thus giving 5.7 g of 2-(4-methylphenyl)-4-phenylquinazoline as a crude product. Then 4.4 g of the compound thus obtained, 2.7 g of NBS and 0.2 g of benzoyl peroxide were suspended in 50 ml of carbon tetrachloride and refluxed with heating for 2 hours. The reaction mixture was allowed to cool and 20 ml of diethyl ether was added thereto. The crystals precipitated were separated by filtration. The filtrate was concentrated under reduced pressure. The residue was recrystallized from chloroform-n-hexane to provide 1.9 g of 2-(4-bromomethylphenyl)-4-phenylquinazoline as colorless needles. Then 1.9 g of the crystals thus obtained were suspended in 10 ml of triethyl phosphite and heated with stirring at 130° C. for 2 hours. After completion of the reaction, an excess of triethyl phosphite was distilled off under reduced pressure and the residue was purified by silica gel column chromatography (eluent: chloroform: n-hexane=1:1) and recrystallized from diethyl ether-n-hexane to provide 0.2 g of the objective compound as colorless needles. Table 1 shows the structure and physical property (melting point) of the compound.

EXAMPLES 40–42

The compounds set forth in Table 1 were prepared in the same manner as in Example 39. Table 1 also shows the structures and physical properties (melting points) of these compounds.

EXAMPLE 43

Preparation of ethyl 4-(6-bromo-4-methoxyquinazolin-2-yl) benzylphosphonate

A 0.9 g quantity of the compound obtained in Example 13 and 0.9 g of lithium bromide were suspended in 30 ml of dry acetonitrile and refluxed with heating for 20 hours. After completion of the reaction, the reaction mixture was allowed to cool and the precipitate was collected by filtration, washed with acetonitrile twice, added to 10 ml of 3N hydrochloric acid and stirred at room temperature for 10 minutes. A 10 ml portion of distilled water was added thereto and the crystals precipitated was collected by filtration and washed with water, thus giving 0.1 g of the objective compound as colorless crystals. Table 1 shows the structure and physical property (melting point) of the compound.

EXAMPLES 44–50

The compounds set forth in Table 1 were prepared in the same manner as in Example 43. Table 1 also shows the structures and physical properties (melting points) of these compounds. Table 2 shows the results of $^1$H-NMR analysis of some compounds.

EXAMPLE 51

Preparation of diethyl 4-(6-bromo-4-mercaptoquinazolin-2-yl)benzylphosphonate

A 10 g quantity of the compound obtained in Example 14 and 4.5 g of Lawesson's reagent were suspended in 80 ml of toluene and refluxed with heating for 1 hour. After completion of the reaction, the solvent was distilled off under reduced pressure and the residue was purified by silica gel column chromatography (eluent: chloroform: methanol= 30:1) and recrystallized from chloroform-n-hexane to provide 7.6 g of the objective compound as light yellow crystals. Table 1 shows the structure and physical property (melting point) of the compound thus obtained.

EXAMPLE 52

Preparation of diethyl 4-(6-bromo-4-mercaptoquinazolin-2-yl)benzyl(thio)phosphonate A 3.0 g quantity of the compound obtained in Example 14 and 3.0 g of Lawesson's reagent were suspended in 20 ml of toluene and refluxed with heating for 2 hours. The reaction mixture was concentrated under reduced pressure and the residue was purified by silica gel column chromatography (eluent: chloroform) and recrystallized from chloroform-n-hexane to provide 2.2 g of the objective compound as yellow crystals (melting point: 196°–199° C.).

EXAMPLE 53

Preparation of diethyl 4-(6-bromo-4-methylthioquinazolin-2-yl)benzyl(thio)phosphonate A 0.60 g quantity of the compound obtained in Example 52 was dissolved in 10 ml of THF, and 0.2 ml of triethylamine and 0.1 ml of methyl iodide were serially added thereto with stirring at room temperature. The stirring was continued at room temperature for 30 minutes. After adding 30 ml of water, the reaction mixture was extracted with chloroform. The chloroform layer was washed with water, dried over sodium sulfate and concentrated under reduced pressure. The residue was purified by silica gel column chromatography (eluent: chloroform: n-hexane=2:1) and recrystallized from diethyl ether-n-hexane to provide 0.43 g of the objective compound as yellow crystals (melting point: 126°–127° C.).

EXAMPLES 54–61

The compounds set forth in Table 3 were prepared in the same manner as in Examples 11 and 12. Table 3 also shows the structures and physical properties (melting points) of these compounds.

Table 2 shows the results of $^1$H-NMR analysis of the compound obtained in Example 57.

EXAMPLE 62

Preparation of diethyl 4-(7-fluoro-4-hydroxyquinazolin-2-yl)benzylphosphonate

A 10 g portion of 2-amino-5-fluorobenzoic acid was dissolved in 100 ml of dichloromethane and 100 ml of pyridine. A solution of 36 g of 4-[(diethoxyphosphoryl)methyl]benzoyl chloride in 50 ml of dichloromethane and 20 ml of DMF was dropwise added with stirring under ice cooling and the stirring was continued at room temperature for 20 hours. After completion of the reaction, the reaction mixture was diluted with 300 ml of dichloromethane and washed serially with diluted hydrochloric acid and saturated sodium bicarbonate. The organic layer was dried over anhydrous magnesium sulfate and the solvent was distilled off under reduced pressure. The residue was recrystallized from dichloromethane-diethylether-n-hexane to provide 17.6 g of diethyl 4-(7-fluoro-4H-3,1-benzoxazin-4-on-2-yl)benzylphosphonate as colorless crystals.

Then 14.3 g of the crystals thus obtained were dissolved in 100 ml of ethanol, and 50 ml of 25% aqueous ammonia was added thereto and stirred at room temperature for 2 hours. After completion of the reaction, the solvent was distilled off to provide the residue containing diethyl 4-[N-(2-carbamoyl-5-fluorophenyl)carbamoyl]benzylphosphonate as colorless powders.

The residue was dissolved in 100 ml of ethanol, and 50 ml of 2N aqueous sodium hydroxide solution was added thereto and stirred at room temperature for 15 hours. The reaction mixture was diluted with 300 ml of dichloromethane. The organic layer was washed with diluted hydrochloric acid and dried over anhydrous magnesium sulfate and the solvent was distilled off under reduced pressure. The residue was recrystallized from dichloromethane-diethyl ether to provide 9.8 g of the objective compound as colorless crystals. Table 3 shows the structure and physical property (melting point) of the compound thus obtained.

EXAMPLES 63–69

The compounds set forth in Table 3 were prepared in the same manner as in Example 62. Table 3 also shows the structures and physical properties (melting points) of these compounds.

EXAMPLE 70

Preparation of diethyl 4-(4-benzyloxy-6,7-dimethoxyquinazolin-2-yl)benzylphosphonate A 4.32 g quantity of the compound obtained in Example 20 was dissolved in 50 ml of anhydrous methanol. A 0.25 g quantity of metal sodium and 1.71 g of benzyl bromide were serially added thereto at room temperature and stirred at 40° C. for 17 hours. The reaction mixture was diluted with 200 ml of dichloromethane and then washed with diluted hydrochloric acid. The organic layer was dried over magnesium sulfate and the solvent was distilled off under reduced pressure. The residue was purified by silica gel column chromatography and the former fraction was recrystallized from dichloromethane-diethyl ether to provide 0.2 g of the objective compound as colorless crystals.

As a by-product, diethyl 4-(3-benzyl-6,7-dimethoxy-4(3H)-quinazolinon-2-yl)benzylphosphonate was obtained from the latter fraction. Table 3 shows the structure and physical property (melting point) of the compound obtained.

EXAMPLES 71–81

The compounds set forth in Table 3 were prepared in the same manner as in Example 70. Table 3 also shows the structures and physical properties (melting points) of these compounds.

TABLE 1

Ph: Phenyl group

| No. | $R^1$ | $R^2$ | $R^3$ | $R^4$ | $R^5$ | Mp (°C.) |
|---|---|---|---|---|---|---|
| 1 | H | H | $-OCH_3$ | $C_2H_5$ | $C_2H_5$ | 85.0–86.0 |
| 2 | H | H | $-OC_2H_5$ | $C_2H_5$ | $C_2H_5$ | 115.0–116.0 |
| 3 | Br | H | $-OCH_3$ | $CH_3$ | $CH_3$ | 93.0–94.0 |
| 4 | Br | H | $-OC_2H_5$ | $C_2H_5$ | $C_2H_5$ | 99.5–100 (dec.) |
| 5 | Br | H | $-OCH(CH_3)_2$ | $C_2H_5$ | $C_2H_5$ | 102–105 |
| 6 | Br | H | $-OC_6H_{13}$ | $C_2H_5$ | $C_2H_5$ | 114–116 |
| 7 | Br | H | $-O-\text{cyclohexyl}$ | $C_2H_5$ | $C_2H_5$ | 96–99 |
| 8 | Br | H | $-OPh$ | $C_2H_5$ | $C_2H_5$ | 141–143 (dec.) |
| 9 | Br | H | $-OCH_2Ph$ | $C_2H_5$ | $C_2H_5$ | 168–171 |
| 10 | Br | H | $-O-(CH_2)_2OPh$ | $C_2H_5$ | $C_2H_5$ | 134–136 |
| 11 | Br | H | $-OCH_3$ | $-CH(CH_3)_2$ | $-CH(CH_3)_2$ | 124.0–125.0 |
| 12 | Br | H | OH | $-CH(CH_3)_2$ | $-CH(CH_3)_2$ | 193.0–194.0 |
| 13 | Br | H | $-OCH_3$ | $C_2H_5$ | $C_2H_5$ | 148.0–149.0 |
| 14 | Br | H | OH | $C_2H_5$ | $C_2H_5$ | 211.0–212.0 |
| 15 | Cl | H | $-OCH_3$ | $C_2H_5$ | $C_2H_5$ | 130.0–130.5 |
| 16 | Cl | H | OH | $C_2H_5$ | $C_2H_5$ | 188.5–189.5 |
| 17 | $NO_2$ | H | $-OCH_3$ | $C_2H_5$ | $C_2H_5$ | 166–170 (dec.) |
| 18 | $NO_2$ | H | OH | $C_2H_5$ | $C_2H_5$ | >250 |
| 19 | $CH_3O-$ | $CH_3O-$ | $-OCH_3$ | $C_2H_5$ | $C_2H_5$ | 138–139 (dec.) |
| 20 | $CH_3O-$ | $CH_3O-$ | OH | $C_2H_5$ | $C_2H_5$ | 185.0–186.0 |
| 21 | H | H | $-NHCH_3$ | $C_2H_5$ | $C_2H_5$ | 165.0–165.5 |
| 22 | H | H | $-NHC_2H_5$ | $C_2H_5$ | $C_2H_5$ | 123.0–124.0 |
| 23 | Br | H | $-NHCH_3$ | $CH_3$ | $CH_3$ | >250 |
| 24 | Br | H | $-NHC_2H_5$ | $CH_3$ | $CH_3$ | >250 |
| 25 | Br | H | $-NHCH_3$ | $C_2H_5$ | $C_2H_5$ | 194.0–195.0 |
| 26 | Br | H | $-NHC_2H_5$ | $C_2H_5$ | $C_2H_5$ | 202.0–203.0 |
| 27 | Br | H | $-NHC_4H_9$ | $C_2H_5$ | $C_2H_5$ | 191–193 |
| 28 | Br | H | $-NH-\text{cyclohexyl}$ | $C_2H_5$ | $C_2H_5$ | 247–249 |
| 29 | Br | H | $-N(\text{pyrrolidinyl})$ | $C_2H_5$ | $C_2H_5$ | 200–202 |

TABLE 1-continued

Structure:

R1, R2 on benzene ring fused to a pyrimidine ring with R3 at position 4 and N=C at position 2 connected to a para-substituted phenyl group: -C6H4-CH2-P(=O)(OR4)(OR5)

Ph: Phenyl group

| No. | R¹ | R² | R³ | R⁴ | R⁵ | Mp (°C.) |
|---|---|---|---|---|---|---|
| 30 | Br | H | -N(piperidine) | $C_2H_5$ | $C_2H_5$ | 146~148 |
| 31 | Br | H | -NHNH₂ | $C_2H_5$ | $C_2H_5$ | 194~198 |
| 32 | Br | H | -NHCH₃ | -CH(CH₃)₂ | -CH(CH₃)₂ | 222~223 (dec.) |
| 33 | Br | H | -NHC₂H₅ | -CH(CH₃)₂ | -CH(CH₃)₂ | 212~213 (dec.) |
| 34 | Cl | H | -NHCH₃ | $C_2H_5$ | $C_2H_5$ | 188.0~189.0 |
| 35 | CH₃O— | CH₃O— | -NHCH₃ | $C_2H_5$ | $C_2H_5$ | >250 |
| 36 | Br | H | -SC₂H₅ | $C_2H_5$ | $C_2H_5$ | 95.0~96.0 |
| 37 | Br | H | -SCH₃ | $C_2H_5$ | $C_2H_5$ | 120~122 |
| 38 | Br | H | -SPh | $C_2H_5$ | $C_2H_5$ | 135~138 |
| 39 | H | H | Ph | $C_2H_5$ | $C_2H_5$ | 139.5~140.5 |
| 40 | Br | H | Ph | CH₃ | CH₃ | 171.0~172.0 |
| 41 | Cl | H | Ph | CH₃ | CH₃ | 158~159 (dec.) |
| 42 | Cl | H | Ph | $C_2H_5$ | $C_2H_5$ | 151.5~152.5 |
| 43 | Br | H | -OCH₃ | $C_2H_5$ | H | 198~200 (dec.) |
| 44 | Br | H | -OC₂H₅ | $C_2H_5$ | H | >250 |
| 45 | Br | H | -Ph | $C_2H_5$ | H | 250 (dec.) |
| 46 | Br | H | -NHCH₃ | $C_2H_5$ | H | 240 (dec.) |
| 47 | Br | H | -NHC₂H₅ | $C_2H_5$ | H | >250 |
| 48 | Br | H | -N(piperidine) | $C_2H_5$ | H | 127~129 |
| 49 | Br | H | -N(CH₃)₂ | $C_2H_5$ | H | 92~94 (dec.) |
| 50 | Br | H | -SC₂H₅ | $C_2H_5$ | H | 205~207 (dec.) |
| 51 | Br | H | SH | $C_2H_5$ | $C_2H_5$ | 155~156 (dec.) |

TABLE 2

| No. | ¹H-NMR (δ: ppm, Internal standard: TMS) |
|---|---|
| 18 | 1.29(t, J=6.9, 6H), 3.28(d, J=21.8, 2H), 4.0-4.1(m, 2H), 7.4-7.5(m, 2H), 7.91(d, J=8.9, 1H), 8.09(d, J=7.4, 2H), 8.5-8.6(m, 1H), 9.14(d, J=2.5, 1H) [CDCl₃-CD₃OD] |
| 23 | 3.13(d, J=4.5, 3H), 3.15(d, J=21.8, 2H), 3.51(s, 3H), 3.55(s, 3H), 7.39(dABq, J=2.0, 7.4, 2H), 7.69(ABq, J=8.9, 1H), 7.87(dABq, J=2.0, 8.9, 1H), 8.40(ABq, J=7.4, 2H), 8.48(d, J=2.0, 1H) [DMSO-d₆] |
| 24 | 1.33(t, J=7.2, 3H), 3.24(d, J=22.0, 2H), 3.54(s, 3H), 3.58(s, 3H), 3.7-3.9(m, 2H), 7.49(ABq, J=8.2, 2H), 7.92(ABq, J=8.5, 1H), 8.04(ABq, J=8.5, 1H), 8.36(ABq, J=8.2, 2H), 8.71(s, 1H), 9.5(br.s, 1H), [DMSO-d₆] |
| 35 | 1.26(t, J=6.9, 6H), 3.24(d, J=21.8, 2H), 3.25(d, J=5.0, 3H), 3.9-4.1(m, 4H), 3.99(s, 3H), 4.03(s, 3H), 5.6-5.7(br.q, 1H), 6.96(s, 1H), 7.29(s, 1H), 7.40(dABq, J=2.5, 8.4, 2H), 8.49(ABq, J=8.4, 2H) [CDCl₃] |
| 44 | 1.17(t, J=6.9, 3H), 1.52(t, J=7.2, 3H), 3.18(d, J=21.8, 2H), 3.8-4.0(m, 2H), 4.76(q, J=7.2, 2H), 7.45(dABq, J=2.0, 7.9, 2H), 7.90(ABq, J=8.9, 1H) 8.07(dABq, J=2.5, 8.9, 1H), 8.26(d, J=2.5, 1H), 8.43(ABq, J=7.9, 2H) [DMSO-d₆] |
| 47 | 1.3(br.t, 3H), 1.4(br.t, 3H), 3.26(d, J=22.0, 2H), 3.9-4.0(m, 2H), 4.0-4.1(m, 2H), 7.5-7.6(m, 2H), 7.9-8.1(m, 1H), 8.18(d, J=8.9, 1H), 8.36(d, J=7.4, 2H), 8.63(s, 1H) [CDCl₃-CD₃OD] |
| 57 | 3.27(d, J=22.3, 2H), 3.71(d, J=10.9, 6H), 4.04(s, 6H), 7.24(s, 1H), 7.50(dd, J=2.5, 8.4, 2H), |

TABLE 2

| No. $^1$H-NMR (δ: ppm, Internal standard: TMS) |
| --- |
| 5 |
| 7.64(s, 1H), 8.14(d, J=7.9, 2H), 11.0(br, 1H) [CDCl$_3$] |

TABLE 3

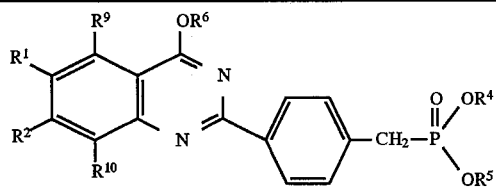

| No. | R$^1$ | R$^2$ | R$^4$ | R$^5$ | R$^6$ | R$^9$ | R$^{10}$ | Mp (°C.) |
| --- | --- | --- | --- | --- | --- | --- | --- | --- |
| 54 | H | H | Et | Et | CH$_3$ | F | H | 80~81 |
| 55 | H | H | Et | Et | H | F | H | 172~173 |
| 56 | —OCH$_3$ | —OCH$_3$ | CH$_3$ | CH$_3$ | CH$_3$ | H | H | 138~139 |
| 57 | —OCH$_3$ | —OCH$_3$ | CH$_3$ | CH$_3$ | H | H | H | 230 以上 |
| 58 | —OCH$_3$ | —OCH$_3$ | iPr | iPr | CH$_3$ | H | H | 133~134 |
| 59 | —OCH$_3$ | —OCH$_3$ | iPr | iPr | H | H | H | 190~191 |
| 60 | H | Cl | Et | Et | CH$_3$ | H | H | 106~107 |
| 61 | H | Cl | Et | Et | H | H | H | 209~211 |
| 62 | H | F | Et | Et | H | H | H | 184~186 |
| 63 | H | H | Et | Et | H | H | H | 187~189 |
| 64 | H | H | CH$_3$ | CH$_3$ | H | H | H | 199~200 |
| 65 | H | H | Et | Et | H | Cl | H | 192~193 |
| 66 | H | CF$_3$ | Et | Et | H | H | H | 210 (dec.) |
| 67 | CH$_3$ | H | Et | Et | H | H | H | 198.5~200 |
| 68 | H | NO$_2$ | Et | Et | H | H | H | 252~254 |
| 69 | H | Cl | Et | Et | H | Cl | H | 263.5~264.5 |
| 70 | —OCH$_3$ | —OCH$_3$ | Et | Et | —CH$_2$Ph | H | H | 141~142 |
| 71 | Br | H | Et | Et | —CH$_2$—(2-F,4-Br-phenyl) | H | H | 101~102 |
| 72 | Br | H | Et | Et | —CH$_2$COOH | H | H | 170 (dec.) |
| 73 | —OCH$_3$ | —OCH$_3$ | Et | Et | —CH$_2$CH=CH$_2$ | H | H | 109~110 |
| 74 | —OCH$_3$ | —OCH$_3$ | iPr | iPr | —CH$_2$Ph | H | H | 123 (dec.) |
| 75 | —OCH$_3$ | —OCH$_3$ | iPr | iPr | —CH$_2$CH$_2$Ph | H | H | 150 (dec.) |
| 76 | —OCH$_3$ | —OCH$_3$ | Et | Et | —CH$_2$COOCH$_3$ | H | H | 86~87 |
| 77 | —OCH$_3$ | —OCH$_3$ | Et | Et | —CH$_2$—(2-F,4-Br-phenyl) | H | H | 145~146 |
| 78 | H | H | Et | Et | —CH$_2$Ph | F | H | 109~110 |
| 79 | H | Cl | Et | Et | —CH$_2$Ph | H | H | 105 (dec.) |
| 80 | H | Cl | Et | Et | —CH$_2$COOCH$_3$ | H | H | 80 (dec.) |
| 81 | —OCH$_3$ | —OCH$_3$ | Et | Et | H | H | —OCH$_3$ | 169~170 |

Et: Ethyl group
iPr: Isopropyl group
Ph: Phenyl group

Formulation examples of the compound of the invention are described below.

FORMULATION EXAMPLE 1

Manufacture of tablets

Using the compound obtained in Example 58 as an active ingredient, tablets (1000 tablets) each containing 250 mg of the active ingredient were manufactured according to the following formula.

| Ingredient | Amount (g) |
|---|---|
| Compound of Example 58 | 250 |
| Lactose (product of Japanese pharmacopeia: JP) | 33.5 |
| Corn starch (JP) | 16.5 |
| Carboxymethyl cellulose calcium (JP) | 12.5 |
| Methylcellulose (JP) | 6.0 |
| Magnesium stearate (JP) | 1.5 |
| Total | 320.0 |

According to the above formula, the compound of Example 58, lactose, corn starch and carboxymethyl cellulose calcium were well blended and granulated using an aqueous solution of methyl cellulose. The granulated mixture was passed through a 24-mesh sieve and the granules under the sieve were mixed with magnesium stearate and compression-molded into tablets.

FORMULATION EXAMPLE 2

Manufacture of capsules

Using the compound obtained in Example 19 as an active ingredient, hard gelatin capsules (1000 units) each containing 250 mg of the active ingredient were manufactured according to the following formula.

| Ingredient | Amount (g) |
|---|---|
| Compound of Example 19 | 250 |
| Crystalline cellulose (JP) | 30 |
| Corn starch (JP) | 17 |
| Talc (JP) | 2 |
| Magnesium stearate (JP) | 1 |
| Total | 300 |

Thus, according to the above formula, the ingredients were finely pulverized and the powders obtained were blended to give a homogeneous composition. This composition was filled into proper-sized gelatin capsule shells for oral administration to provide the objective capsules.

FORMULATION EXAMPLE 3

Manufacture of granules

Using the compound obtained in Example 73 as an active ingredient, granules (1000 g) containing 500 mg of the active ingredient in each gram were manufactured according to the following formula.

| Ingredient | Amount (g) |
|---|---|
| Compound of Example 73 | 500 |
| Crystalline cellulose (JP) | 100 |
| Corn starch (JP) | 250 |
| Lactose (JP) | 100 |
| Carboxymethyl cellulose calcium (JP) | 40 |
| Hydroxypropylmethyl cellulose (JP) | 10 |
| Total | 1000 |

Thus, according to the above formula, the compound of Example 73, lactose, corn starch, crystalline cellulose and carboxymethyl cellulose calcium were thoroughly blended and kneaded with an aqueous solution of hydroxypropylmethyl cellulose. The resultant composition was granulated using an extrusion granulator and dried at 50° C. for 2 hours to provide the objective granules.

PHARMACOLOGICAL TEST EXAMPLE 1

Preventive and therapeutic effects of the compound of the invention on hyperlipidemia were determined using rats with Triton-induced hyperlipidemia according to the method of Kuroda et al. [Biochem. Biophys. Acta., 489., 119 (1977)] as follows.

Using 6 to 7-week-old male Wistar rats in groups of 5 (test groups), a solution of 300 mg/kg Triton (Triton WR 1339) in physiological saline was administered into the tail vein and, at the same time, 100 mg/kg of the test compound suspended in a 0.5% CMC-Na solution was administered orally. As a control group, a group of 5 rats given Triton were orally dosed with a 0.5% aqueous CMC-Na solution.

Twenty four hours after administration of Triton, blood was taken from the rats and the plasma total triglyceride was determined using Triglyceride G-Test Wako (product of Wako Pure Chemical Industries, Ltd.). Using the measured values in the control group as references, the rate of decrease (%) in plasma total triglyceride in the test group was calculated by the equation given below. The test rats were deprived of food before Triton administration through completion of blood sampling but allowed free access to drinking water.

$$\text{Rate of decrease (\%)} = \left[ 1 - \frac{\text{(Test group value)}}{\text{(Control group value)}} \right] \times 100$$

TABLE 5

| Test compound (Example No.) | Rate of decrease of triglyceride (%) |
|---|---|
| 19 | 86 |
| 20 | 37 |
| 58 | 81 |
| 59 | 31 |
| 70 | 40 |
| 73 | 71 |

Industrial Applicability

The present invention provides a novel phosphonic diester derivative, which is useful as therapeutic agents for hyperlipidemic diseases, hypertension, diabetes and the like.

We claim:

1. A phosphonic diester compound of the formula:

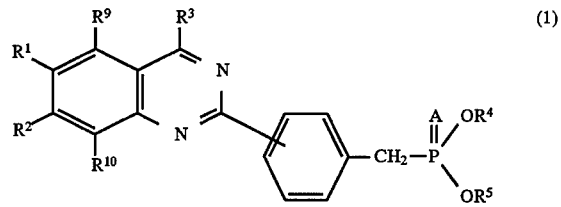

wherein A represents an oxygen atom or a sulfur atom; $R^1$, $R^2$, $R^9$ and $R^{10}$ are the same or different and they each represent a hydrogen atom, an alkoxy group having 1 to 6 carbon atoms, a nitro group, an alkyl group having 1 to 6 carbon atoms, a halogen-substituted alkyl group having 1 to 6 carbon atoms or a halogen atom; $R^3$ represents a phenyl group or —B—$R^6$ (wherein B represents an oxygen atom or a sulfur atom and $R^6$ represents a hydrogen atom, an alkyl group having 1 to 6 carbon atoms, a cycloalkyl group, having 3 to 8 carbon atoms a phenyl group, or a phenyl alkyl group optionally having a halogen atom as a substituent on the phenyl ring, a phenoxy-alkyl group, an alkoxycarbonyl alkyl group, a carboxy alkyl group or alkenyl group) wherein each alkyl moiety has 1 to 6 carbon atoms or —N⁷R⁸ (wherein R⁷ and R⁸ are the same or different and they each represent a hydrogen atom, an alkyl group having 1 to 6 carbon atoms, an amino group or a cycloalkyl group or combinedly represent an alkylene group having 1 to 6 carbon atoms); and R⁴ and R⁵ are the same or different and they each represent a hydrogen atom or an alkyl group having 1 to 6 carbon atoms.

2. A phosphonic diester compound of the formula:

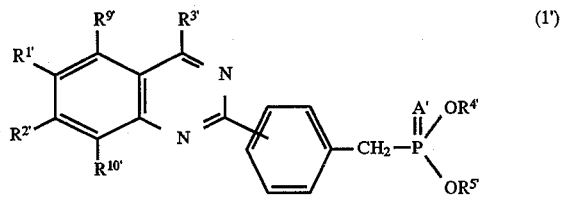

(1')

wherein A' represents an oxygen atom or a sulfur atom; R¹' represents a hydrogen atom, an alkoxy group having 1 to 6 carbon atoms, a nitro group or a halogen atom; R²' represents a hydrogen atom, an alkoxy group having 1 to 6 carbon atoms, an alkyl group having 1 to 6 carbon atoms, a halogen-substituted alkyl group having 1 to 6 carbon atoms or a halogen atom; R³' represents a phenyl group, —O—R⁶ (wherein R⁶ represents a hydrogen atom, a alkyl group having 1 to 6 carbon atoms, a cycloalkyl group having 3 to 8 carbon atoms, a phenyl group, a phenyl alkyl group wherein said alkyl group has 1 to 6 carbon atoms optionally having a halogen atom as a substituent on the phenyl ring, a phenoxy alkyl group wherein said alkyl group has 1 to 6 carbon atoms, an alkoxy carbonyl alkyl group wherein said alkyl moieties have 1 to 6 carbon atoms, a carboxy alkyl group wherein said alkyl group has 1 to 6 carbon atoms or an alkenyl group having 2 to 1 to 6 carbon atoms, —S—R⁶' (wherein R⁶' represents a hydrogen atom, an alkyl group having 1 to 6 carbon atoms or a phenyl group) or —NR⁷R⁸ (wherein R⁷ and R⁸ are the same or different and they each represent a hydrogen atom, an alkyl group having 1 to 6 carbon atoms, an amino group or a cycloalkyl group having 3 to 8 carbon atoms or combinedly represent an alkylene group having 1 to 6 carbon atoms); R⁴' represents an alkyl group having 1 to 6 carbon atoms; R⁵' represents a hydrogen atom or an alkyl group having 1 to 6 carbon atoms; R⁹' represents a hydrogen atom or a halogen atom; and R¹⁰' represents a hydrogen atom or an alkoxy group having 1 to 6 carbon atoms.

3. The phosphonic diester compound of claim 2 which is represented by the formula 1' wherein R¹' and R²' each represent an alkoxy group having 1 to 6 carbon atoms; R³' represents —O—R⁶ wherein R⁶ represents a hydrogen atom, an alkyl group having 1 to 6 carbon atoms, or a cycloalkyl group having from 3 to 8 carbon atoms, a phenyl group, a phenyl alkyl group wherein said alkyl moiety has 1 to 6 carbon atoms optionally having a halogen atom as a substituent on the phenyl ring, a phenoxy alkyl group wherein said alkyl group has 1 to 6 carbon atoms, an alkoxy carbonyl alkyl group wherein said alkyl moieties have 1 to 6 carbon atoms, a carboxy alkyl group wherein said alkyl group has 1 to 6 carbon atoms or a alkenyl group having 2 to 6 carbon atoms; A' represents an oxygen group; and R⁴' and R³' each represent an alkyl group having 1 to 6 carbon atoms.

4. The phosphonic diester compound of claim 2 which is represented by the formula 1' wherein R⁹' and R¹⁰' each represent a hydrogen atom and R³' represents a hydroxy group, an alkoxy group having 1 to 6 carbon atoms, a phenyl alkoxy group wherein said alkoxy group has 1 to 6 carbon atoms or a alkenyloxy group wherein said alkenyloxy group has 2 to 6 carbons atoms.

5. The phosphonic diester compound of claim 4 which is a compound selected from the class consisting of (1) diethyl 4-(4-hydroxy-6,7-dimethoxyquinazolin-2-yl) benzylphosphonate, (2) diisopropyl 4-(4-hydroxy-6,7-dimethoxyquinazolin-2-yl)benzylphosphonate, (3) diethyl 4-(4,6,7-trimethoxyquinazolin-2-yl)benzylphosphonate, (4) diisopropyl 4-(4,6,7-trimethoxyquinazolin-2-yl)benzylphosphonate, (5) diethyl 4-(4-benzyloxy-6,7-dimethoxyquinazolin-2-yl)benzylphosphonate and (6) diethyl 4-(4-allyloxy-6,7-dimethoxyquinazolin-2-yl)benzylphosphonate.

6. The phosphonic diester compound of claim 5 which is diethyl 4-(4,6,7-trimethoxyquinazolin-2-yl)benzylphosphonate or diisopropyl 4-(4,6,7-trimethoxyquinazolin-2-yl)benzylphosphonate.

7. An antihyperlipidemic composition comprising the phosphonic diester compound claimed in any one of the claims 1 through 6 as an active ingredient.

8. A method of treating hyperlipidemia which comprises administering to a patient a pharmacologically effective amount of the antihyperlipidemic composition of claim 7.

* * * * *